United States Patent [19]

Parravicini et al.

[11] Patent Number: 4,581,449
[45] Date of Patent: Apr. 8, 1986

[54] PROCESS OF MAKING ETHYL{6-[ETHYL-(2-HYDROXYPROPYL)AMINO]-3-PYRIDAZINYL}HYDRAZINECARBOXYLATE

[75] Inventors: Francesco Parravicini, Milan; Mario Pinza, Corsico, both of Italy

[73] Assignee: I.S.F. S.p.A., Milan, Italy

[21] Appl. No.: 600,406

[22] Filed: Apr. 16, 1984

[30] Foreign Application Priority Data

Apr. 28, 1983 [IT]  Italy ........................ 20814 A/83

[51] Int. Cl.[4] ............................................ C07D 237/20
[52] U.S. Cl. .................... 544/224; 544/183; 544/236
[58] Field of Search ................... 544/224, 183

[56] References Cited

PUBLICATIONS

Stanovnik & Tisler, Journal of Heterocyclic Chemistry, 1969, 6(3), 413–14.
Zupan et al, Journal of Organic Chemistry, 37(19), pp. 2960–2963, (1972).
March, "Advanced Organic Chemistry", 2nd Edition, pp. 353, 598, 806.

*Primary Examiner*—Donald G. Daus
*Assistant Examiner*—Robert Benson
*Attorney, Agent, or Firm*—Wenderoth, Lind & Ponack

[57] ABSTRACT

A novel method of preparing ethyl{6-[ethyl-(2-hydroxypropyl)amino]-3-pyridazinyl}hydrazinecarboxylate is disclosed, wherein 7-chloro-3-methyl-4-oxo-4H-pyridazino[6,1-c][1,2,4]triazine is treated with ethyl-(2-hydroxypropyl)amine. The corresponding amino derivative is hydrolized in mild conditions and the hydrazino compound thus obtained is suitably acylated.

4 Claims, No Drawings

PROCESS OF MAKING ETHYL{6-[ETHYL-(2-HYDROXYPROPYL)AMINO]-3-PYRIDAZINYL}HYDRAZINECARBOXYLATE

BACKGROUND OF THE INVENTION

1. Field of the Invention

This invention relates to a method of preparing a pyridazinic structure compound, namely ethyl{6-[ethyl-(2-hydroxypropyl-amino)-3-pyridazinyl}hydrazinecarboxylate. Such a compound, has a marked and lasting anti-hypertensive activity and causes retention of neither sodium nor liquids in the patients treated with it.

SUMMARY OF THE INVENTION

The method of this invention affords ethyl {6-[ethyl-(2-hydroxypropyl)amino]-3-pyridazinyl}hydrazine carboxylate with good yields by reactions which occur in very mild conditions from readily available starting material.

It has been now observed that the introduction of the amino group in place of a halogen atom in a pyridazino[6,1-c][1,2,4]triazinic derivative may be effected by heating in a suitable solvent at temperatures in the 80° C. to 110° C. range, and that from the corresponding amino derivative it is possible to obtain the corresponding hydrazinopyridazine derivative by means of a mildly acidic hydrolysis. By acylaltion of the resulting compound, ethyl{6-[ethyl-(2-hydroxypropyl)amino]-3-pyridazinyl}hydrazinecarboxylate is obtained.

The method as a whole may be synthesized as follows,

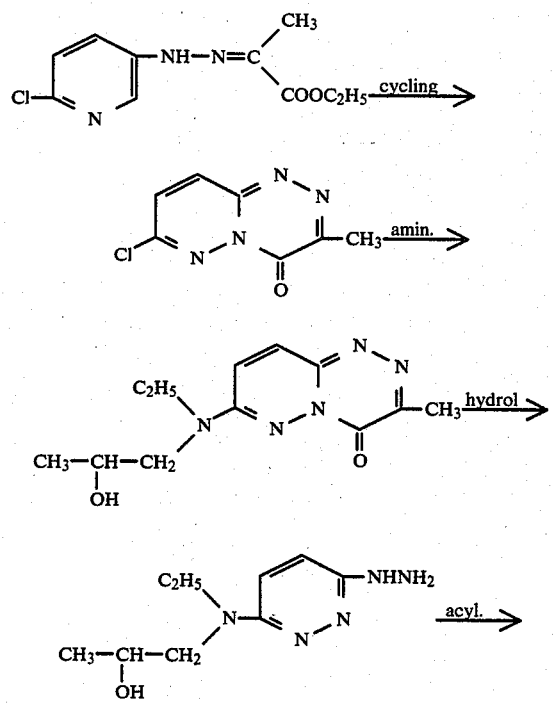

-continued

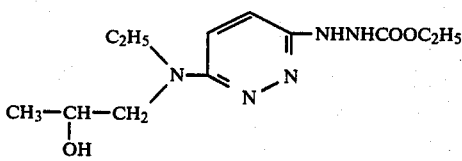

DETAILED DESCRIPTION OF THE PREFERRED EMBODIMENT

The Example which follows is directed to better illustrate the invention in a non-limitative way.

EXAMPLE

Ethyl{6-[ethyl(2-hydroxypropyl)amino]-3-pyridazinyl} hydrazinecarboxylate 20 grams of 3-(α-carboethoxyethylhydrazino)-6-chloropyridazine are heated to 115° C. with 240 g polyphosphoric acid for about 30 minutes, thereafter the resulting solution is chilled in ice and to the vitreous mass 700 g ice are added, the pH of the mixture being raised to 4 with the addition of 200 ml ammonium hydroxide. The precipitate is washed with water and is crystallized from acetone, to yield 9.7 g 7-chloro-3-methyl-4-oxo-4H-pyridazino[6,1c][1,2,4]triazine which melts at 151° C. (with decomposition).

A solution comprising 480 mg 7-chloro-3-methyl-4-oxo-4H-pyridazino[6,1-c][1,2,4]triazine and 510 mg ethyl-(2-hydroxypropyl)amine in 10 ml toluene is heated to reflux for two hours, toluene is removed by evaporation, the remaining part if taken up with acetone, filtered, and the filtrate concentrated to a small volume. After cooling, 400 mg 7-[ethyl-(2-hydroxypropyl)amino]-3-methyl-4-oxo-4H-pyridazino[6,1-c][1,2,4]triazine are collected under a vacuum, which melts at 140°–145° C. 1.3 grams 7-[ethyl-(2-hydroxypropyl)amino]-3-methyl-4-oxo-4H-pyridazino[6,1-c][1,2,4]triazine and 1 gram 2,4-dinitrophenylhydrazine are heated, while stirring, to 60° C. for three hours in 60 ml of 15% hydrochloric acid. These are cooled to 0° C. overnight, collected under a vacuum and washed with cold water. The mother liquors, after filtering, are evaporated to a dry condition, the residue being taken up twice with n.butylic alcohol and each time re-evaporated. A solid product is obtained which is triturated with 10 ml n.butylic alcohol, cooled, and collected under vacuum to yield 1 g of 3-[ethyl-(2-hydroxypropyl)amino]-6-hydrazinopyridazine dihydrochloride melting (with decomposition) at 212° C.

Added carfully while stirring in a nitrogen atomsphere, to a solution comprising 1.4 g of 3-[ethyl-(2-hydroxypropyl)amino]-6-hydrazinopyridazine dihydrochloride in 20I ml water and 10 ml isopropylic alcohol are 1.7 g potassium bicarbonate. Dripped into the reaction mixture, maintained at 0° C., is 5.9 g ethyl chlorocarbonate over one hour, thereafter the reaction is allowed to proceed at room temperature for two hours, the mixture is maintained at 0° C. overnight, and the precipitate is collected under a vacuum which is washed with cold water to yield 0.7 g ethyl{6-[ethyl-(2-hydroxypropyl)amino]-3-pyridazinyl}hydrazinecarboxylate melting at 158°–162° C.

We claim:

1. A process for preparing a compound of Structure I

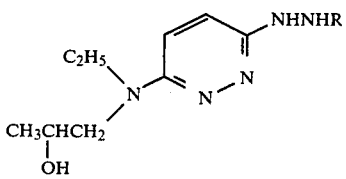

wherein R is hydrogen or COOC$_2$H$_5$ which comprises:
(a) reacting 7-chloro-3-methyl-4-oxo-4H-pyridaziono-[6,1-c] [1,2,4]triazine with N-ethyl-N-(2-hydroxypropyl)-amine, to obtain a compound of Structure II

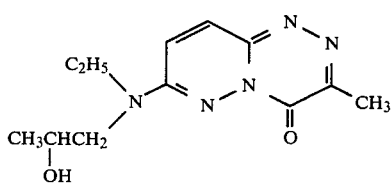

(b) hydrolyzing the compound of Structure II under mild acidic conditions, and in the presence of 2,4-dinitrophenyl hydrazine and optionally converting the resulting compounds of Structure I in which R is H into the compound in which R is COOC$_2$H$_5$.

2. A process according to claim 1 in which the hydrolysis is carried out in dilute aqueous hydrochloric acid.

3. A process according to claim 1 in which 7-[ethyl(2-hydroxypropyl)amino]-3-methyl-4-oxo-4H-pyridazino-[6,1-c] [1,2,4]triazine is hydrolyzed in dilute hydrochloric acid and the 3-[ethyl(2-hydroxypropyl)amino]-6-hydrazinopyridazine obtained is acylated with ethyl chlorocarbonate to give ethyl (6-[ethyl(2-hydroxypropyl)amino]-3-pyridazinyl)-hydrazinocarboxylate.

4. A compound of Structure (II)

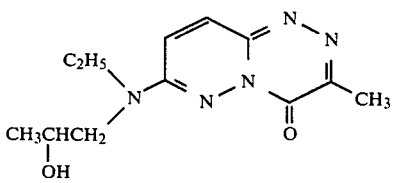

* * * * *